(12) United States Patent
Pariseau

(10) Patent No.: US 10,352,844 B2
(45) Date of Patent: Jul. 16, 2019

(54) MULTIPLE PARTICLE SENSORS IN A PARTICLE COUNTER

(71) Applicant: Particles Plus, Inc., Canton, MA (US)

(72) Inventor: David Pariseau, Los Altos, CA (US)

(73) Assignee: Particles Plus, Inc., Canton, MA (US)

( * ) Notice: Subject to any disclaimer, the term of this patent is extended or adjusted under 35 U.S.C. 154(b) by 0 days.

(21) Appl. No.: 14/214,876

(22) Filed: Mar. 15, 2014

(65) Prior Publication Data

US 2014/0268144 A1 Sep. 18, 2014

Related U.S. Application Data

(60) Provisional application No. 61/786,642, filed on Mar. 15, 2013.

(51) Int. Cl.
*G01N 15/14* (2006.01)
*G01N 15/00* (2006.01)

(52) U.S. Cl.
CPC . *G01N 15/1459* (2013.01); *G01N 2015/0046* (2013.01); *G01N 2015/1486* (2013.01); *G01N 2015/1493* (2013.01)

(58) Field of Classification Search
CPC combination set(s) only.
See application file for complete search history.

(56) References Cited

U.S. PATENT DOCUMENTS

| | | | |
|---|---|---|---|
| 5,257,087 A * | 10/1993 | Furuya | G01N 15/0205 356/335 |
| 6,016,194 A * | 1/2000 | Girvin | G01N 15/0211 356/335 |
| 6,327,918 B1 | 12/2001 | Lawless | |
| 7,439,855 B1 | 10/2008 | Yufa | |
| 7,457,709 B2 | 11/2008 | Zhang et al. | |
| 7,724,150 B2 | 5/2010 | Chandler et al. | |
| 7,895,000 B2 | 2/2011 | Chandler et al. | |
| 7,973,929 B2 | 7/2011 | Bates | |
| 9,070,272 B2 | 6/2015 | Gettings et al. | |
| 9,116,121 B2 | 8/2015 | Kaye et al. | |
| 9,140,638 B2 | 9/2015 | Pariseau et al. | |
| 9,140,639 B2 | 9/2015 | Pariseau | |
| 9,141,094 B2 | 9/2015 | Pariseau et al. | |
| 9,157,847 B2 | 10/2015 | Pariseau et al. | |
| 9,158,652 B2 | 10/2015 | Pariseau | |
| 9,541,475 B2 | 1/2017 | Chu et al. | |
| 9,677,990 B2 | 6/2017 | Pariseau et al. | |

(Continued)

FOREIGN PATENT DOCUMENTS

| GB | 2420616 A | 5/2006 |
|---|---|---|
| GB | 2474235 A | 4/2011 |

(Continued)

OTHER PUBLICATIONS

US 5,424,397 A1, 04/2013, Fjerdingstad (withdrawn)

(Continued)

*Primary Examiner* — Tri T Ton

(74) *Attorney, Agent, or Firm* — McCarter & English, LLP

(57) ABSTRACT

An airborne, gas, or liquid particle sensor with multiple particle sensor blocks in a single particle counter. Each sensor would sample a portion of the incoming airstream, or possibly a separate airstream. The various counters could be used separately or in concert.

4 Claims, 3 Drawing Sheets

(56) References Cited

U.S. PATENT DOCUMENTS

| | | |
|---|---|---|
| 2004/0068389 A1 | 4/2004 | Kleefstra |
| 2006/0071803 A1 | 4/2006 | Hamburger et al. |
| 2008/0246963 A1* | 10/2008 | Nakajima .......... G01N 15/0205 |
| | | 356/336 |
| 2010/0253509 A1 | 10/2010 | Fu et al. |
| 2014/0281476 A1 | 9/2014 | Pariseau |
| 2015/0323941 A1 | 11/2015 | Pariseau et al. |
| 2017/0336312 A1 | 11/2017 | Stoeber et al. |

FOREIGN PATENT DOCUMENTS

| | | |
|---|---|---|
| WO | 2008/140816 A1 | 11/2008 |
| WO | 2014/043413 A1 | 3/2014 |
| WO | 2016/065465 A1 | 5/2016 |

OTHER PUBLICATIONS

Chung et al., Comparison of real-time instruments used to monitor airborne particulate matter. J Air Waste Manag Assoc. Jan. 2001;51(1):109-20.

Esmen et al., Theoretical Investigation of the Interrelationship Between Stationary and Personal Sampling in Exposure Estimation. Applied Occupational and Environmental Hygiene. 2000;15(1):114-119.

\* cited by examiner

MULTIPLE PARTICLE SENSORS IN A PARTICLE COUNTER

CROSS-REFERENCE TO RELATED APPLICATION

This application claims priority to U.S. Provisional Application Ser. No. 61/786,642 filed on Mar. 15, 2013, titled MULTIPLE PARTICLE SENSORS IN A PARTICLE COUNTER by inventors David Pariseau, the entire disclosure of which is hereby incorporated herein by reference.

This application is related to and incorporates by reference U.S. Non-Provisional application Ser. No. 14/214,899, filed herewith on Mar. 15, 2014, titled PARTICLE COUNTER WITH INTEGRATED BOOTLOADER by inventor David Pariseau; U.S. Non-Provisional application Ser. No. 14/214,870, filed herewith on Mar. 15, 2014, titled PERSONAL AIR QUALITY MONITORING SYSTEM by inventors David Pariseau and Adam Giandomenico; U.S. Non-Provisional application Ser. No. 14/214,903, filed herewith on Mar. 15, 2014, titled MIXED-MODE PHOTO-AMPLIFIER FOR PARTICLE COUNTER by inventors David Pariseau and Ivan Horban; U.S. Non-Provisional application Ser. No. 14/214,889, filed herewith on Mar. 15, 2014, titled INTELLIGENT MODULES IN A PARTICLE COUNTER by inventor David Pariseau; U.S. Non-Provisional application Ser. No. 14/214,895, filed herewith on Mar. 15, 2014, titled PULSE SCOPE FOR PARTICLE COUNTER by inventor David Pariseau; and U.S. Non-Provisional application Ser. No. 14/214,907, filed herewith on Mar. 15, 2014, titled PULSE DISCRIMINATOR FOR PARTICLE COUNTER by inventors David Pariseau and Ivan Horban.

BACKGROUND

Particle counters have been used for decades in manufacturing or industrial applications to measure particulate quantities in air, gases or liquids. Typically such counters would also bin particulates by size. These size bins vary by application and often by instrument. A particle counter has at least one size channel and popular counters can have 6 or more channels. Typically these size channels discriminate pulses based on the pulse height of the incoming signal. The pulse height refers to the peak voltage of the signal. Sometimes there is also rudimentary discrimination of pulse width, often in hardware.

These systems provide a go/no-go qualification for an incoming pulse, typically they are implemented in hardware and provide a simple gate function such that pulses below a minimum duration are excluded from counting. The intent is to reject noise, typically at the most sensitive resolution where the signal-to-noise ratio is the poorest. However such particle counters are limited in their scope of particle size they can detect, are difficult to calibrate and don't have a means for detecting equipment failure. Therefore, what is needed is a system and method that allows detection of a wide range of particle sizes that is easy to calibrate and determine failures.

SUMMARY

In accordance with various aspects and teachings of the present invention, a system and method are provided that allow detection of a wide range of particle sizes. The foregoing is a summary and includes, by necessity, simplifications, generalizations and omissions of detail. Those skilled in the art will appreciate that the summary is illustrative only and is not intended to be in any way limiting.

BRIEF DESCRIPTION OF THE DRAWINGS

The foregoing summary as well as the following detailed description is better understood when read in conjunction with the appended drawings. For the purpose of illustrating the invention, there is shown in the drawings exemplary constructions of the invention; however, the invention is not limited to the specific various aspects, embodiments, methods and instrumentalities disclosed in the drawings.

DETAILED DESCRIPTION

Figure 1:
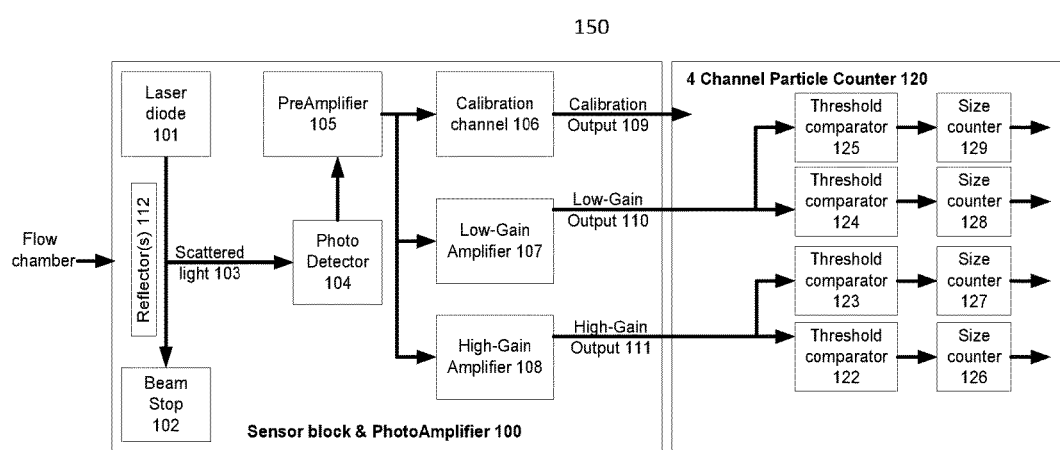
FIG. 1 shows a system in accordance with the various aspects of the present invention.

It is noted that, as used in this description, the singular forms "a," "an" and "the" include plural referents unless the context clearly dictates otherwise. Reference throughout this specification to "one aspect," "another aspect," "at least one aspect," "various aspects," "further aspect," "one embodiment," "an embodiment," "certain embodiments," or similar language means that a particular aspect, feature, structure, or characteristic described in connection with the embodiment or embodiments is included in at least one aspect or embodiment of the present invention. Thus, appearances of the phrases "in accordance with one aspect," "in accordance with various aspects," "in accordance another aspect," "one embodiment," "in at least one embodiment," "in an embodiment," "in certain embodiments," and similar language throughout this specification may, but do not necessarily, all refer to the same embodiment.

In accordance with the various aspects of the present invention, a device includes a computing device. As referred to herein, the devices may be part of a system or the system. It may be implemented to include a central processing unit (e.g., a processor), memory, input devices (e.g., keyboard and pointing devices), output devices (e.g., display devices), and storage device (e.g., disk drives). The memory and storage device are computer-readable media that may contain instructions or code that, when executed by the processor or the central processing unit, cause the device to perform certain tasks. In addition, data structures and message structures may be stored or transmitted via a data transmission medium, such as a signal on a communications link. Various communications channels may be used (e.g., the Internet, a local area network (LAN), a wide area network (WAN), or a point-to-point dial-up connection, or any other wireless channel or protocol) to create a link.

In accordance with the various aspects of the present invention, the device or system may be use various computing systems or devices including personal computers, server computers, hand-held or laptop devices, multiprocessor systems, microprocessor based systems, programmable consumer electronics, network personal computers (PCs), minicomputers, mainframe computers, distributed computing environments that include any of the above systems or devices, and the like. In accordance with the various aspects of the present invention, the device or system may also provide its services to various computing systems such as personal computers, cell phones, personal digital assistants, consumer electronics, home automation devices, and so on.

In accordance with the various aspects of the present invention, the device or system may be described in the general context of computer-executable instructions, such as program modules or code, which is executed by one or more computers or devices. Generally, program modules include routines, programs, objects, components, data structures, and so on that perform particular tasks or implement particular data types. Typically, the functionality of the program modules may be combined or distributed as desired in various embodiments.

Where a range of values is provided, it is understood that each intervening value, to the tenth of the unit of the lower limit unless the context clearly dictates otherwise, between the upper and lower limit of that range and any other stated or intervening value in that stated range, is encompassed within the aspects of the present invention. The upper and lower limits of these smaller ranges may independently be included in the smaller ranges and are also encompassed within the aspects of the present invention, subject to any specifically excluded limit in the stated range. Where the stated range includes one or both of the limits, ranges excluding either or both of those included limits are also included in the aspects of the present invention.

Referring now to FIG. 1, an example of a four-channel particle counter front-end 150 is shown below. In this example a beam present between the laser diode (101) and the beam stop (102) scatters light (103) as particles cross that beam. Typically the scattered light (103) is focused by one or more reflectors (112) onto the face of a photo-diode (104) on a photo-amplifier board (100). The tiny current in the photo-diode is then pre-amplified, usually by a trans-impedance amplifier (105). The pre-amplified signal is usually available on a calibration channel (106) for use during calibration. The pre-amplifier (105) signal is also sent to one or more amplifiers. In this case there are two, a low-gain channel (107) and a high-gain channel (108).

These amplifiers further increase the signal amplitude and transmit send it, often, to a separate particle counting board (120). On this board the incoming pulse signals are sorted into size bins. In this example there are four channels, two channels (122,123) connected to the high-gain amplifier (111) and two channels (124,125) connected to the low-gain amplifier (110). The threshold comparators (122,123,124, 125) are setup during the calibration phase so that they each channel counts pulses above some threshold. This can be a manual process with manual adjustment of a potentiometer, or a programmatic process where firmware would set a digital potentiometer or digital-to-analog converter. The counter outputs (126,127,128,129) would then be read by microcontroller and displayed to the user.

A similar system functions for gases other than air, and liquids. It also functions for counters that use a light-blocking rather than a light-scattering architecture, except that pulses in light-blocking systems see a decrease in light as the particles pass through the beam.

Traditionally, only a single sensor block and photo-amplifier board (100) is used in an instrument. This is largely due to the cost, and complexity of these sub-assemblies which often make-up the bulk of the cost of an instrument. It is also due to the processing requirements on the counter board.

With the advent of miniaturization, lower-cost components, increases in processing power the possibility of combining multiple particle sensor blocks into a single instrument becomes possible.

In certain embodiments, a counter includes multiple sensor block/photo-amplifier sub-assemblies within a single counter instrument. Each of these blocks would be communicatively coupled, e.g. connected, to a common counter board, or alternatively each of these blocks could have individual counter interface boards which might then provide processed data to a common instrument board which would manage the display, and external interfaces.

In certain embodiments, the airstream is split into multiple segments, each with a respective sensor block. Such an embodiment means that:

the particle velocity is slowed for each sensor given a fixed sample volume, this means that the system gets more signal per particle and thus can develop a more sensitive instrument (on all channels);

the system can use a count comparator to correlate counts between multiple sensors, which would allows for:

failure notification, since one failed sensor will mean a loss of count uniformity, calibration notification, since count uniformity will degrade, and redundancy, ability for remaining sensors to estimate counts for a failed sensor; and the system can assign different sensors for different size ranges, and end-up with a sensor with a much larger dynamic range.

In certain embodiments, separate sensor blocks sample different airstreams. For example, instruments with multiple sensors can:

check that filtration is working as expected. By sampling air from either side of the filter simultaneously, the system can check that particulate counts from two or more sensors reflect a functioning filter;

check that manufacturing equipment is operating as expected. By sampling air from various areas around a particular piece of equipment, the system can ensure that particulate levels are what is expected. Doing so with a single instrument allows us to correlate these counts and make decisions that involve more than a single threshold; and allow for an upgrade path for manifold systems that currently share a sensor block and switch airstreams between samples, sharing a single block, which means that there is no continuous sampling of all channels. By replacing this with a counter multiple chambers, the manifold installation could be made continuous, at a lower cost than providing individual instruments for each channel.

Figure 2:
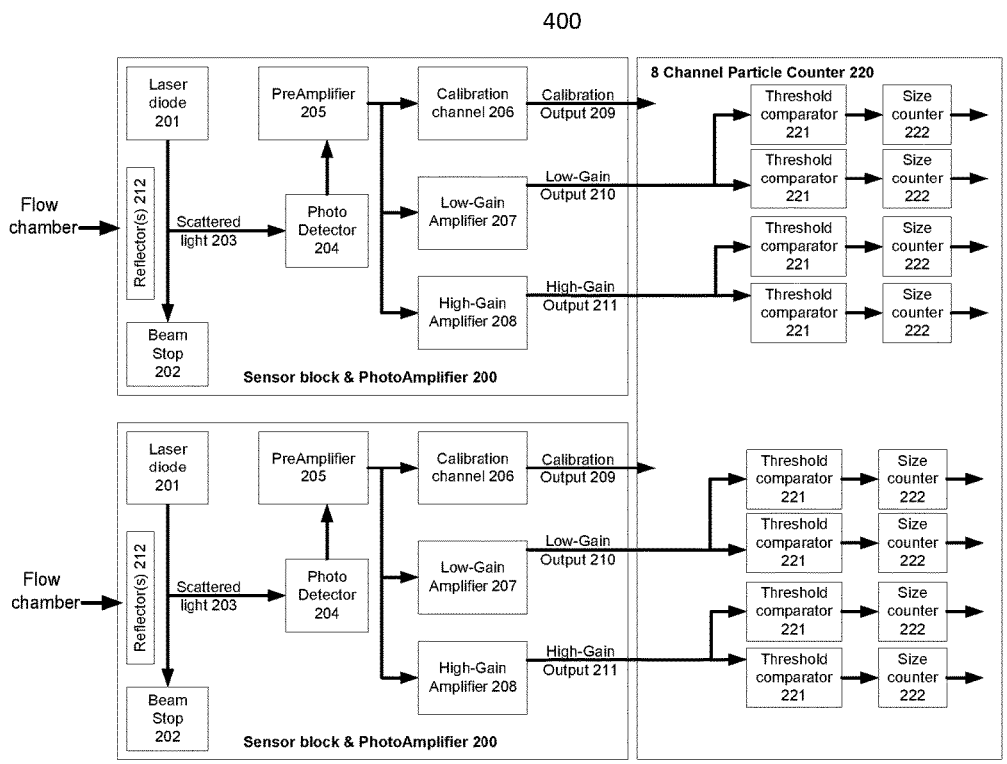
FIG. 2 shows a system in accordance with the various aspects of the present invention.

Referring now to FIG. 2, one such architecture, shown below as system 400, would provide two or more sensor blocks (200) having process the Gain Outputs (210,211), the two or more sensor blocks (200) being communicatively coupled to a common counter board (220) which would implement the threshold comparators (221) and counters (222).

Figure 3:
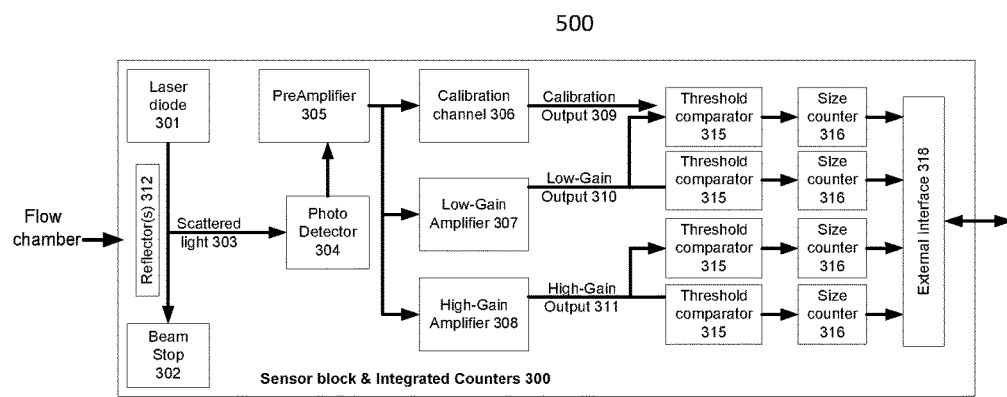
FIG. 3 shows a system in accordance with the various aspects of the present invention.

Referring now to FIG. 3, an alternative architecture is shown as system 500, based on the figure below, system 500 provides two or more of these sensor blocks combined with integrated counters (300). These Output Gain channels (307, 308) would interface to on-board Threshold comparators (315) and then to on-board Counters (316). These would be managed and accessed via an external interface (318). This interface could be any number of things, from a microcontroller with some type of standard interface like UART, SPI, I2C, UNIO, PMP, etc. to a custom interface like a memory mapped I/O interface for an off-board controller.

Regardless of the actual interface used, an off-board system would be used to setup and access the counter data for local processing, manipulation, display, etc. or to communicate this data to an external system.

Another option would be to have the sensor block have local processing beyond the typical Threshold Comparator and Counter implementation, such that pulse-height was measured for each pulse, and perhaps other parameters like pulse-width, time-of-arrival, etc. With such local processing it would allow the creation of intelligent sensors that could have a configurable number of channels, each with configurable thresholds.

And, going the other way, the sensors could simply consist of the sensor chamber, the light components, photo-detector and pre-amplifier with everything else being integrated into one or more printed circuit boards.

In certain embodiments, a single block could be created with multiple chambers in it, each with its own light source (or they could use a shared light source split from one laser and routed to each chamber) and then a single printed circuit board with all the electronics for the entire instrument.

In certain embodiments, more than one chamber is present in an instrument to provide enhanced or otherwise unavailable performance or functionality and that the information from these chambers is processed by one or more sub-systems within the instrument and/or forwarded to some external system for post-processing, analysis, reporting, etc.

While various embodiments have been described above, it should be understood that they have been presented by way of example only, not limitation, and various changes in form and details may be made. Any portion of the device, instrument, apparatus and/or methods described herein may be combined in any combination, except mutually exclusive combinations. The aspects and embodiments described herein can include various combinations and/or sub-combinations of the functions, components and/or features of the different embodiments described. For example, multiple, distributed processing systems can be configured to operate in parallel.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

It will be apparent that various aspects of the present invention as related to certain embodiments may be implemented in software, hardware, application logic, or a combination of software, hardware, and application logic. The software, application logic and/or hardware may reside on a server, an electronic device, or be a service. If desired, part of the software, application logic and/or hardware may reside on an electronic device and part of the software, application logic and/or hardware may reside on a remote location, such as server.

In accordance with the aspects disclosed in the teachings of the present invention and certain embodiments, a program or code may be noted as running on a device, an instrument, a system, or a computing device, all of which are an article of manufacture. Additional examples of an article of manufacture include: a server, a mainframe computer, a mobile telephone, a multimedia-enabled smartphone, a tablet computer, a personal digital assistant, a personal computer, a laptop, or other special purpose computer each having one or more processors (e.g., a Central Processing Unit, a Graphical Processing Unit, or a microprocessor) that is configured to execute a computer readable program code (e.g., an algorithm, hardware, firmware, and/or software) to receive data, transmit data, store data, or perform tasks and methods. Furthermore, an article of manufacture (e.g., device) includes a non-transitory computer readable medium having a series of instructions, such as computer readable program steps or code, which is encoded therein. In certain aspects and embodiments, the non-transitory computer readable medium includes one or more data repositories, memory, and storage, including non-volatile memory. The non-transitory computer readable medium includes corresponding computer readable program or code and may include one or more data repositories. Processors access the computer readable program code encoded on the corresponding non-transitory computer readable mediums and execute one or more corresponding instructions. Other hardware and software components and structures are also contemplated.

Unless defined otherwise, all technical and scientific terms used herein have the same meaning as commonly understood by one of ordinary skill in the art to which this invention belongs. Although any methods and materials similar or equivalent to those described herein can also be used in the practice of the present invention, representative illustrative methods and materials are described herein.

All publications and patents cited in this specification are herein incorporated by reference as if each individual publication or patent were specifically and individually indicated to be incorporated by reference and are incorporated herein by reference to disclose and describe the methods and/or system in connection with which the publications are cited. The citation of any publication is for its disclosure prior to the filing date and should not be construed as an admission that the present invention is not entitled to ante-date such publication by virtue of prior invention. Further, the dates of publication provided may be different from the actual publication dates which may need to be independently confirmed.

All statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A particle counting instrument comprising:
   at least two particle sensors, each comprising:
      at least one light source focused into a beam;
      at least one photo-detector in spatial proximity to the beam, where the photo-detector detects changes in light as airborne particulates pass through the beam;
      at least one amplifier in communication with the photo-detector, the amplifier converts signals from the photo-detector into electrical pulses;
      at least one threshold comparator that provides an output count pulse when the photo-detector pulse exceeds a configurable threshold voltage, the output count pulse representing a particular particle size channel; and
      at least one particle counter that accumulates the output pulse counts from the at least one threshold comparator,
   wherein the particle sensors have separate airstreams, and wherein at least one of the separate airstreams is through tubing to provide sampling of environments other than that of the particle counting instrument.

2. The particle counting instrument in claim 1, wherein at least two particle sensors are setup with identical particulate size channels in order to provide at least one of redundancy and validation.

3. The particle counting instrument in claim 1, wherein each particle sensor is responsible for a portion of particle size spectrum and wherein dividing up the particle size spectrum allows each particle sensor to have the amplification of the at least one amplifier optimized for smaller particle range.

4. The particle counting instrument in claim 1, wherein the particle sensors have separate airstreams divided from a common inlet and wherein the divided airstreams re-combine after passing through the particle sensors to share a common exhaust.

\* \* \* \* \*

UNITED STATES PATENT AND TRADEMARK OFFICE
CERTIFICATE OF CORRECTION

PATENT NO. : 10,352,844 B2
APPLICATION NO. : 14/214876
DATED : July 16, 2019
INVENTOR(S) : David Pariseau It is certified that error appears in the above-identified patent and that said Letters Patent is hereby corrected as shown below:

On the Title Page

Item (60):
Replace "Provisional application No. 61/786,642 filed on Mar. 15, 2013." with -Provisional Application No. 61/786,616 filed on Mar. 15, 2013, Provisional application No. 61/786,642 filed on Mar. 15, 2013, Provisional Application No. 61/786,651 filed on Mar. 15, 2013, Provisional Application No. 61/786,658 filed on Mar. 15, 2013 and Provisional Application No. 61/786,667 filed on Mar. 15, 2013.-

In the Specification

Column 1, Line 7:
Replace "This application claims priority to U.S. Provisional Application Ser. No. 61/786,642 filed on Mar. 15, 2013, titled MULTIPLE PARTICLE SENSORS IN A PARTICLE COUNTER by inventors David Pariseau, the entire disclosure of which is hereby incorporated herein by reference.
    This application is related to and incorporates by reference U.S. Non-Provisional application Ser. No 14/214,899, filed herewith on Mar. 15, 2014, titled PARTICLE COUNTER WITH INTEGRATED BOOTLOADER by inventor David Pariseau; U.S. Non-Provisional application Ser. No. 14/214,870, filed herewith on Mar. 15, 2014, titled PERSONAL AIR QUALITY MONITORING SYSTEM by inventors David Pariseau and Adam Giandomenico; U.S. Non-Provisional application Ser. No. 14/214,903, filed herewith on Mar. 15, 2014, titled MIXED-MODE PHOTO-AMPLIFIER FOR PARTICLE COUNTER by inventors David Pariseau and Ivan Horban; U.S. Non-Provisional application Ser. No. 14/214,889, filed herewith on Mar. 15, 2014, titled INTELLIGENT MODULES IN A PARTICLE COUNTER by inventor David Pariseau; U.S. Non-Provisional application Ser. No. 14/214,895, filed herewith on Mar. 15, 2014, titled PULSE SCOPE FOR PARTICLE COUNTER by inventor David Pariseau; and U.S. Non-Provisional application Ser. No. 14/214,907, filed herewith on Mar. 15, 2014, titled PULSE DISCRIMINATOR FOR PARTICLE COUNTER by inventors David Pariseau and Ivan Horban." with
-This application claims priority to U.S. Provisional Application Ser. No. 61/786,642 filed on Mar. 15, 2013, titled MULTIPLE PARTICLE SENSORS IN A PARTICLE COUNTER by inventor David Signed and Sealed this
Sixth Day of July, 2021

Drew Hirshfeld
*Performing the Functions and Duties of the
Under Secretary of Commerce for Intellectual Property and
Director of the United States Patent and Trademark Office*

Pariseau, the entire disclosure of which is hereby incorporated herein by reference, and this application also claims priority to U.S. Provisional Patent Application Ser. No. 61/786,616, filed on Mar. 15, 2013, titled PARTICLE COUNTER WITH INTEGRATED BOOTLOADER by inventor David Pariseau,, U.S. Provisional Patent Application Ser. No. 61/786,651, filed on Mar. 15, 2013, titled INTELLIGENT MODULES IN A PARTICLE COUNTER by inventor David Pariseau, U.S. Provisional Patent Application Ser. No. 61/786,658, filed on Mar. 15, 2013, titled PULSE SCOPE FOR PARTICLE COUNTER by inventor David Pariseau, and U.S. Provisional Patent Application Ser. No. 61/786,667, filed on Mar. 15, 2013, titled PERSONAL AIR QUALITY MONITORING SYSTEM by inventors David Pariseau and Adam Giandomenico.

This application is related to and incorporates by reference U.S. Non-Provisional application Ser. No. 14/214,899, filed herewith on Mar. 15, 2014, titled PARTICLE COUNTER WITH INTEGRATED BOOTLOADER by inventor David Pariseau; U.S. Non-Provisional application Ser. No. 14/214,903, filed herewith on Mar. 15, 2014, titled MIXED-MODE PHOTO-AMPLIFIER FOR PARTICLE COUNTER by inventors David Pariseau and Ivan Horban; U.S. Non-Provisional application Ser. No. 14/214,889, filed herewith on Mar. 15, 2014, titled INTELLIGENT MODULES IN A PARTICLE COUNTER by inventor David Pariseau; U.S. Non-Provisional application Ser. No. 14/214,895, filed herewith on Mar. 15, 2014, titled PULSE SCOPE FOR PARTICLE COUNTER by inventor David Pariseau; and U.S. Non-Provisional application Ser. No. 14/214,907, filed herewith on Mar. 15, 2014, titled PULSE DISCRIMINATOR FOR PARTICLE COUNTER by inventors David Pariseau and Ivan Horban.-